(12) United States Patent
Salter et al.

(10) Patent No.: US 9,694,739 B2
(45) Date of Patent: Jul. 4, 2017

(54) DISINFECTING HANDLE

(71) Applicant: Ford Global Technologies, LLC, Dearborn, MI (US)

(72) Inventors: Stuart C. Salter, White Lake, MI (US); Paul Kenneth Dellock, Northville, MI (US); James J. Surman, Cliton Township, MI (US); Bhavani Thota, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 94 days.

(21) Appl. No.: 14/937,139

(22) Filed: Nov. 10, 2015

(65) Prior Publication Data

US 2017/0129396 A1    May 11, 2017

(51) Int. Cl.
| | |
|---|---|
| *B60Q 1/00* | (2006.01) |
| *B60Q 1/26* | (2006.01) |
| *B60Q 3/00* | (2017.01) |
| *B60Q 3/02* | (2006.01) |
| *F21V 9/16* | (2006.01) |
| *F21V 19/00* | (2006.01) |
| *A61L 2/08* | (2006.01) |
| *F21Y 101/02* | (2006.01) |

(52) U.S. Cl.
CPC .............. *B60Q 3/008* (2013.01); *A61L 2/088* (2013.01); *B60Q 3/0233* (2013.01); *F21V 9/16* (2013.01); *F21V 19/0015* (2013.01); *F21Y 2101/02* (2013.01)

(58) Field of Classification Search
CPC .. A61L 2/088; A61L 2/10; B60Q 1/26; B60Q 1/2619; B60Q 1/2661; B60Q 1/2669; B60Q 1/2696; B60Q 3/00; B60Q 3/20; B60Q 3/217; B60Q 3/267; B60Q 3/68; F21V 9/16; F21V 19/0015
USPC ................................ 362/487, 501, 509–510
See application file for complete search history.

(56) References Cited

U.S. PATENT DOCUMENTS

| | | | |
|---|---|---|---|
| 5,053,930 | A | 10/1991 | Benavides |
| 5,709,453 | A | 1/1998 | Krent et al. |
| 5,839,718 | A | 11/1998 | Hase et al. |
| 6,031,511 | A | 2/2000 | DeLuca et al. |
| 6,117,362 | A | 9/2000 | Yen et al. |
| 6,414,213 | B2 | 7/2002 | Ohmori |
| 6,419,854 | B1 | 7/2002 | Yocom et al. |
| 6,494,490 | B1 | 12/2002 | Trantoul |
| 6,577,073 | B2 | 6/2003 | Shimizu et al. |
| 6,729,738 | B2 | 5/2004 | Fuwausa et al. |
| 6,737,964 | B2 | 5/2004 | Samman et al. |

(Continued)

FOREIGN PATENT DOCUMENTS

| | | |
|---|---|---|
| CN | 1869381 A | 11/2006 |
| CN | 101337492 A | 1/2009 |

(Continued)

*Primary Examiner* — Jason Moon Han
(74) *Attorney, Agent, or Firm* — Jason Rogers; Price Heneveld LLP (57) ABSTRACT

A vehicle handle assembly is provided that includes a light-producing-assembly with a first light source and a second light source. The first and second light sources are configured to emit light of different wavelengths. A photoluminescent structure is configured to luminesce in response to excitation by light emitted by the first light source and a phosphorescent structure is configured to phosphoresce in response to excitation by light emitted by the second light source.

19 Claims, 5 Drawing Sheets

(56) References Cited

U.S. PATENT DOCUMENTS

| | | |
|---|---|---|
| 6,773,129 B2 | 8/2004 | Anderson, Jr. et al. |
| 6,820,888 B1 | 11/2004 | Griffin |
| 6,851,840 B2 | 2/2005 | Ramamurthy et al. |
| 6,859,148 B2 | 2/2005 | Miller |
| 6,871,986 B2 | 3/2005 | Yamanaka et al. |
| 6,953,536 B2 | 10/2005 | Yen et al. |
| 6,990,922 B2 | 1/2006 | Ichikawa et al. |
| 7,161,472 B2 | 1/2007 | Strumolo et al. |
| 7,213,923 B2 | 5/2007 | Liu et al. |
| 7,216,997 B2 | 5/2007 | Anderson, Jr. |
| 7,264,366 B2 | 9/2007 | Hulse |
| 7,264,367 B2 | 9/2007 | Hulse |
| 7,441,914 B2 | 10/2008 | Palmer et al. |
| 7,501,749 B2 | 3/2009 | Takeda et al. |
| 7,575,349 B2 | 8/2009 | Bucher et al. |
| 7,635,212 B2 | 12/2009 | Seidler |
| 7,745,818 B2 | 6/2010 | Sofue et al. |
| 7,753,541 B2 | 7/2010 | Chen et al. |
| 7,834,548 B2 | 11/2010 | Jousse et al. |
| 7,862,220 B2 | 1/2011 | Cannon et al. |
| 7,987,030 B2 | 7/2011 | Flores et al. |
| 8,016,465 B2 | 9/2011 | Egerer et al. |
| 8,022,818 B2 | 9/2011 | la Tendresse et al. |
| 8,066,416 B2 | 11/2011 | Bucher |
| 8,071,988 B2 | 12/2011 | Lee et al. |
| 8,097,843 B2 | 1/2012 | Agrawal et al. |
| 8,136,425 B2 | 3/2012 | Bostick |
| 8,163,201 B2 | 4/2012 | Agrawal et al. |
| 8,178,852 B2 | 5/2012 | Kingsley et al. |
| 8,197,105 B2 | 6/2012 | Yang |
| 8,203,260 B2 | 6/2012 | Li et al. |
| 8,207,511 B2 | 6/2012 | Bortz et al. |
| 8,232,533 B2 | 7/2012 | Kingsley et al. |
| 8,247,761 B1 | 8/2012 | Agrawal et al. |
| 8,286,378 B2 | 10/2012 | Martin et al. |
| 8,408,766 B2 | 4/2013 | Wilson et al. |
| 8,415,642 B2 | 4/2013 | Kingsley et al. |
| 8,421,811 B2 | 4/2013 | Odland et al. |
| 8,466,438 B2 | 6/2013 | Lambert et al. |
| 8,519,359 B2 | 8/2013 | Kingsley et al. |
| 8,519,362 B2 | 8/2013 | Labrot et al. |
| 8,552,848 B2 | 10/2013 | Rao et al. |
| 8,606,430 B2 | 12/2013 | Seder et al. |
| 8,624,716 B2 | 1/2014 | Englander |
| 8,631,598 B2 | 1/2014 | Li et al. |
| 8,664,624 B2 | 3/2014 | Kingsley et al. |
| 8,683,722 B1 | 4/2014 | Cowan |
| 8,724,054 B2 | 5/2014 | Jones |
| 8,754,426 B2 | 6/2014 | Marx et al. |
| 8,773,012 B2 | 7/2014 | Ryu et al. |
| 8,846,184 B2 | 9/2014 | Agrawal et al. |
| 8,876,352 B2 | 11/2014 | Robbins et al. |
| 8,952,341 B2 | 2/2015 | Kingsley et al. |
| 9,006,751 B2 | 4/2015 | Kleo et al. |
| 9,018,833 B2 | 4/2015 | Lowenthal et al. |
| 9,057,021 B2 | 6/2015 | Kingsley et al. |
| 9,065,447 B2 | 6/2015 | Buttolo et al. |
| 9,187,034 B2 | 11/2015 | Tarahomi et al. |
| 9,299,887 B2 | 3/2016 | Lowenthal et al. |
| 2002/0159741 A1 | 10/2002 | Graves et al. |
| 2002/0163792 A1 | 11/2002 | Formoso |
| 2003/0167668 A1 | 9/2003 | Fuks et al. |
| 2003/0179548 A1 | 9/2003 | Becker et al. |
| 2004/0213088 A1 | 10/2004 | Fuwausa |
| 2006/0087826 A1 | 4/2006 | Anderson, Jr. |
| 2006/0097121 A1 | 5/2006 | Fugate |
| 2007/0032319 A1 | 2/2007 | Tufte |
| 2007/0285938 A1 | 12/2007 | Palmer et al. |
| 2007/0297045 A1 | 12/2007 | Sakai et al. |
| 2009/0219730 A1 | 9/2009 | Syfert et al. |
| 2009/0251920 A1 | 10/2009 | Kino et al. |
| 2009/0260562 A1 | 10/2009 | Folstad et al. |
| 2009/0262515 A1 | 10/2009 | Lee et al. |
| 2011/0012062 A1 | 1/2011 | Agrawal et al. |
| 2012/0001406 A1 | 1/2012 | Paxton et al. |
| 2012/0104954 A1 | 5/2012 | Huang |
| 2012/0183677 A1 | 7/2012 | Agrawal et al. |
| 2012/0280528 A1 | 11/2012 | Dellock et al. |
| 2013/0335994 A1 | 12/2013 | Mulder et al. |
| 2014/0029281 A1 | 1/2014 | Suckling et al. |
| 2014/0065442 A1 | 3/2014 | Kingsley et al. |
| 2014/0103258 A1 | 4/2014 | Agrawal et al. |
| 2014/0264396 A1 | 9/2014 | Lowenthal et al. |
| 2014/0266666 A1 | 9/2014 | Habibi |
| 2014/0373898 A1 | 12/2014 | Rogers et al. |
| 2015/0046027 A1 | 2/2015 | Sura et al. |
| 2015/0109602 A1 | 4/2015 | Martin et al. |
| 2015/0138789 A1 | 5/2015 | Singer et al. |
| 2015/0267881 A1 | 9/2015 | Salter et al. |
| 2016/0016506 A1 | 1/2016 | Collins et al. |
| 2016/0236613 A1 | 8/2016 | Trier |

FOREIGN PATENT DOCUMENTS

| | | |
|---|---|---|
| CN | 201169230 Y | 2/2009 |
| CN | 201193011 Y | 2/2009 |
| CN | 202023408 U | 11/2011 |
| CN | 204127823 U | 1/2015 |
| CN | 204152305 U | 2/2015 |
| DE | 4120677 A1 | 1/1992 |
| DE | 29708699 U1 | 7/1997 |
| DE | 10319396 A1 | 11/2004 |
| EP | 1793261 A1 | 6/2007 |
| EP | 2778209 A1 | 9/2014 |
| JP | 2000159011 A | 6/2000 |
| JP | 2007238063 A | 9/2007 |
| KR | 20060026531 A | 3/2006 |
| WO | 2006047306 A1 | 5/2006 |
| WO | 2014063440 A1 | 5/2014 |
| WO | 2014088298 A1 | 6/2014 |
| WO | 2014115119 A1 | 7/2014 |

DISINFECTING HANDLE

FIELD OF THE INVENTION

The present invention generally relates to vehicle lighting systems and more particularly relates to vehicle lighting systems employing photoluminescent structures.

BACKGROUND OF THE INVENTION

Illumination arising from the use of photoluminescent structures offers a unique and attractive viewing experience. It is therefore desired to implement such structures in automotive vehicles for various lighting applications.

SUMMARY OF THE INVENTION

According to one aspect of the present invention, a vehicle handle assembly is provided that includes a light-producing-assembly with a first light source and a second light source. The first and second light sources are configured to emit light of different wavelengths. A photoluminescent structure is configured to luminesce in response to excitation by light emitted by the first light source and a phosphorescent structure is configured to phosphoresce in response to excitation by light emitted by the second light source.

According to another aspect of the present invention, a vehicle handle assembly is provided that includes a substrate and a light-producing-assembly with first LEDs and second LEDs. The first LEDs configured to emit light of a different wavelength than the second LEDs. A disinfecting layer is activated based on light of at least one of the first and second LEDs.

According to yet another aspect of the present invention, a method of disinfecting a handle is provided that includes the steps of providing a handle with a light-producing-assembly having first LEDs and second LEDs, energizing a disinfecting layer and a phosphorescent structure using light from the second LEDs, and altering a direction of electrical current across the light-producing-assembly to activate the first LEDs and deactivate the second LEDs.

These and other aspects, objects, and features of the present invention will be understood and appreciated by those skilled in the art upon studying the following specification, claims, and appended drawings.

DETAILED DESCRIPTION OF THE PREFERRED EMBODIMENTS

As required, detailed embodiments of the present invention are disclosed herein. However, it is to be understood that the disclosed embodiments are merely exemplary of the invention that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present invention.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Figure 1:
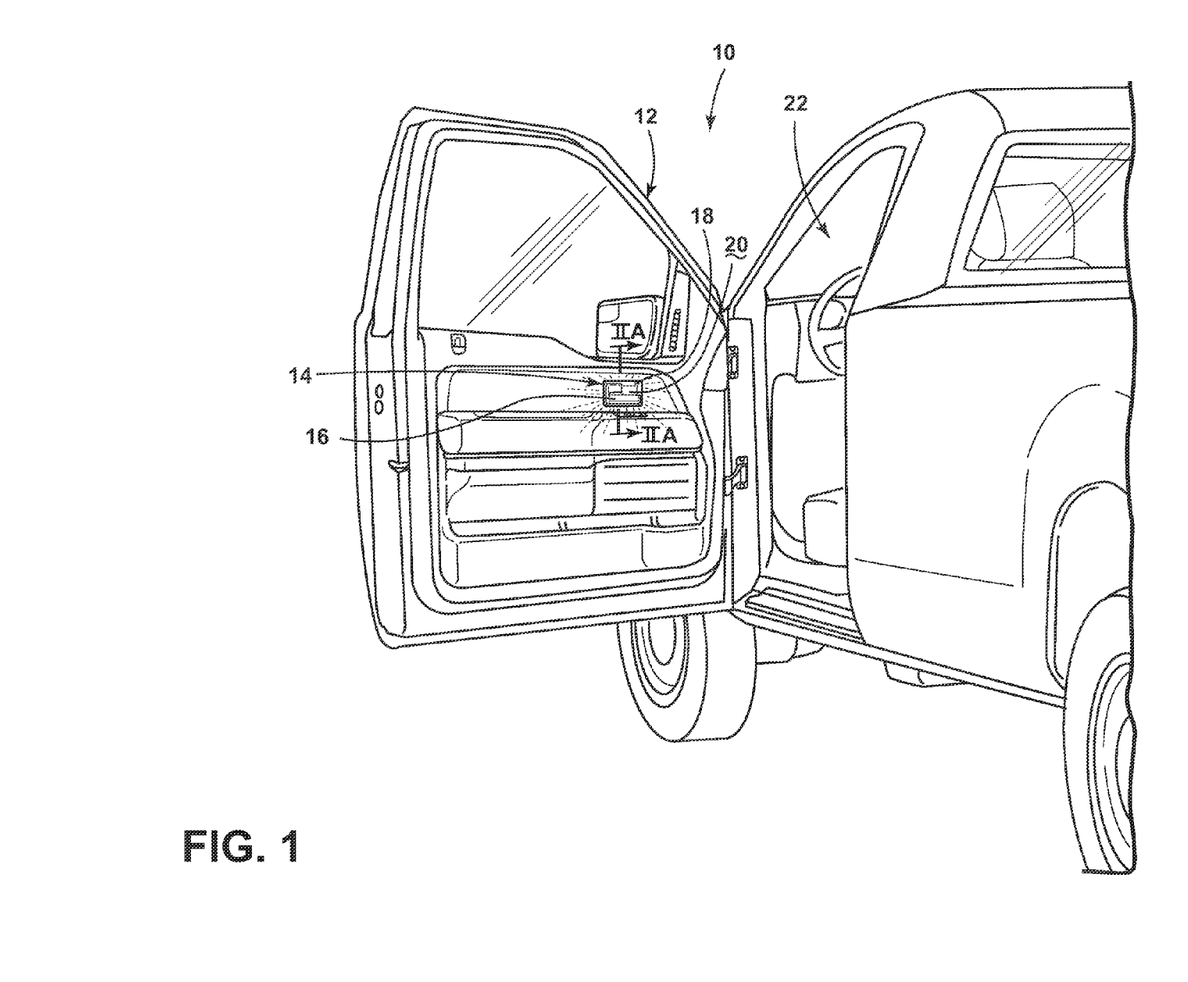
FIG. 1 is a perspective view of a door of a vehicle shown in an open position, according to one embodiment.

Referring to FIG. 1, a vehicle 10 is generally shown having a door 12, according to one embodiment. Positioned on an interior side of the door 12 is an interior handle assembly 14. The handle assembly 14 is configured to be engageable by a hand of a user and may be used to facilitate egress from the vehicle 10 by a passenger or to simply open the door 12. The handle assembly 14 includes a handle 16 and a backing 18. The backing 18 defines a cavity 20 within which the handle 16 is rotatably disposed. The handle 16 and the cavity 20 may be implemented in a variety of configurations and placements within the vehicle 10 (e.g., on a driver side of the vehicle 10, on a passenger side of the vehicle 10, in a rear seat location, and on exterior locations of the vehicle 10) without departing from the spirit of this disclosure. In operation, at least a portion of the handle assembly 14 may produce illumination directed toward an interior 22 of the vehicle 10, as demonstrated by the dashed lines extending from the handle assembly 14. As will be described herein, the illumination originates from a light-producing-assembly disposed within the handle assembly 14 and it is contemplated that the light-producing-assembly may be operated to effectuate a variety of lighting, notification and functional applications.

Figure 2A:
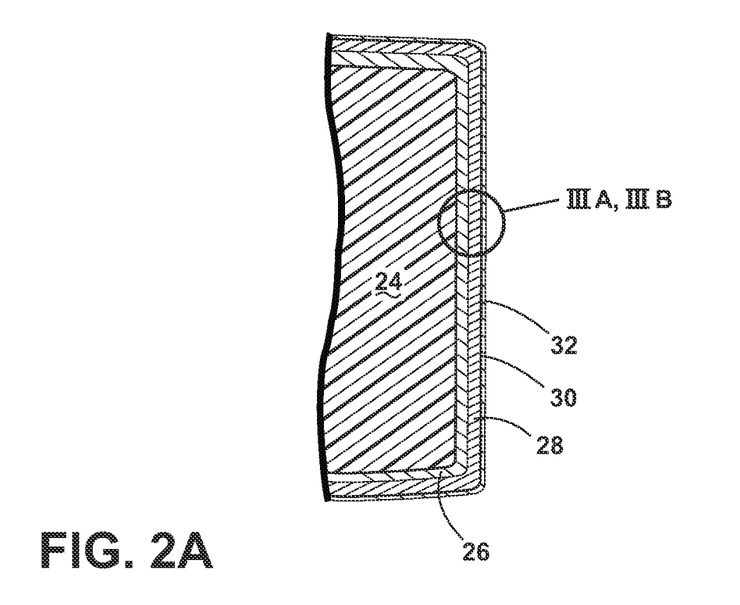
FIG. 2A is an enlarged cross-sectional view of the interior door latch handle assembly depicted in FIG. 1 taken along line II-II of FIG. 1.

Referring to the depicted embodiment of FIG. 2A, the handle 16 of the handle assembly 14 is a multi-layer structure configured to provide both lighting to the handle assembly 14 and a disinfecting functionality to the handle 16. It should be understood that although described in connection with the handle 16 of the handle assembly 14, the following disclosure may equally be applied to other locations on the vehicle 10 that are touched by a user (e.g., the backing 18, other gripping surfaces on the door 12, grab handles located on A-pillars and roof liners, instrument panel handles, glove box handle, exterior handles, other storage compartment handles, seat adjustment handles, gear selection handles, and/or knobs). The handle 16 includes a substrate 24 on which a light-producing-assembly 26 is positioned. The light-producing-assembly 26 is configured to emit light outward from the handle assembly 14 into the interior 22 of the vehicle 10 when the door 12 is in a closed position, substantially closed position, or open position. The handle 16 is depicted as including an optional hiding layer 28 positioned on top of the light-producing-assembly 26. A protective layer 30 is positioned on top of the hiding layer 28 with a disinfecting layer 32 positioned on an opposite side of the protective layer 30 than the hiding layer 28.

The substrate 24 may be an insert molded plastic component or other suitable material to which the light-producing-assembly 26 may be coupled (e.g., via thermal forming and/or adhesively). The hiding layer 28 may be a polymeric coating which has been produced to aid in hiding or obscuring the light-producing-assembly 26 from viewers of the handle assembly 14. The hiding layer 28 may optionally be colored, hazed, or subjected to a vacuum metallization process to aid in the hiding of the light-producing-assembly 26. Positioned on the hiding layer 28 is the protective layer 30. The protective layer 30 may be a plastic or rubber material configured to prevent interaction between the disinfecting layer 32, the light-producing-assembly 26 and/or the hiding layer 28. In one embodiment, the protective layer 30 may be silicone (e.g., polymerized siloxanes or polysiloxanes). In various embodiments, the protective layer 30 may be applied using chemically enhanced plasma deposition, vacuum deposition, cathodic arc deposition, sputtering, physical vapor deposition, other plasma deposition techniques, and/or conventional vacuum coating technology. After deposition, the protective layer 30 forms a hard coat which protects the underlying structure from the disinfecting layer 32. The protective layer 30 may have a thickness in a range between about 1 nm and about 50 nm, between about 5 nm and about 40 nm, or between about 10 nm and about 25 nm. In various embodiments, the protective layer 30 may be substantially transmissive to light emitted from the light-producing-assembly 26. For example, the protective layer 30 may have a transmissivity greater than about 80%, greater than about 90% greater than about 95%, or greater than about 99%. In some embodiments, the protective layer 30 may be variably transmissive (e.g., between about 50% and about 100% transmissive) based on the wavelength of light being passed through the protective layer 30.

Positioned on the protective layer 30 is the disinfecting layer 32. The disinfecting layer 32 may be configured to disinfect or kill bacteria, fungi, viruses and/or pathogens capable of infecting human or animal hosts. Additionally, the disinfecting layer 32 may breakdown organic compounds (e.g., oils and greases) dirt, grime, and other compounds typically present on human hands. The disinfecting layer 32 may be passive, or configured to constantly (e.g., substantially all the time) break down the above noted materials, or may be active and be activated upon the excitation of light (e.g., ultraviolet light) or energy from the light-producing-assembly 26. In some embodiments, the disinfecting layer 32 may always have some minimal level of disinfecting property which may be increased through activation of the light-producing-assembly 26. In various embodiments, activation of the disinfecting layer 32 by the light-producing-assembly 26 may result in the disinfecting layer 32 releasing charged or uncharged hydroxyl radicals which may react with the above noted bacteria, dirt, oils, and other contaminants to create the disinfecting property. The disinfecting layer 32 may include antimicrobial agents such as metal particles (e.g., titanium, cobalt nickel, copper, zinc, zirconium, molybdenum, tin, cerium and/or lead) and oxides thereof in sufficient quantities to have an antimicrobial or antiviral effect. For example, the disinfecting layer 32 may include $TiO_2$, $ZnO$, $CuO$, $SnO_2$ and/or combinations thereof. In various embodiments, the antimicrobial agents of the disinfecting layer 32 may have a size on the order of nano-scale particles (e.g., particles having an average diameter of less than about 1μ, less than about 500 nm, less than about 100 nm, less than about 10 nm, less than about 2 nm, or less than about 1 nm). In one exemplary embodiment, the disinfecting layer 32 may include a plurality of $TiO_2$ nanoparticles which activate and become antimicrobial, antifungal, antiviral, and/or anti-organic upon application of ultraviolet light (e.g., light having a wavelength less than about 375 nm) from the light-producing-assembly 26. The disinfecting layer 32 may be applied via sputter coating, physical vapor deposition, chemical vapor deposition, plasma deposition, vacuum deposition, cathodic arc deposition, other plasma deposition techniques, and/or conventional vacuum coating technology.

Figure 2B:
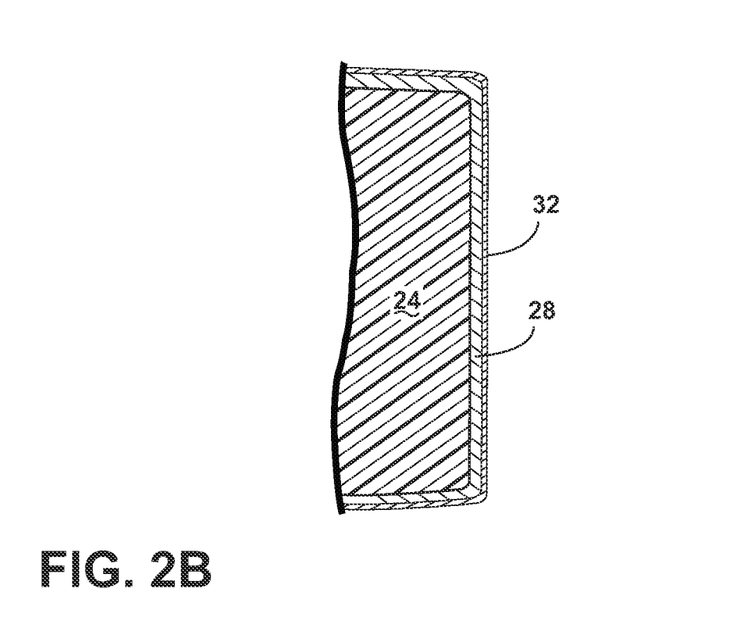
FIG. 2B is a cross-sectional view of an exterior door latch handle assembly.

Referring now to FIG. 2B, the handle assembly 14 may include a handle on the exterior of the vehicle 10 to allow access to the vehicle 10 such as for a driver or passenger. In such an embodiment, the exterior handle may be assembled in substantially the same manner as described in connection with the interior handle 16 of FIG. 2A, but the light-producing-assembly 26 may be optional. A cost savings may be achieved by removing the light-producing-assembly 26 from the handle 16 and allowing an excitation source external to the vehicle 10 (e.g., ultraviolet radiation from the sun or nearby illumination sources) to activate the disinfecting layer 32. In other embodiments, the disinfecting layer 32 may be passive, or constantly disinfecting, as explained above. Additionally, the protective layer 30 may also be optional and the disinfecting layer 32 may be positioned directly on the hiding layer 28 or the substrate 24.

Figure 3A:
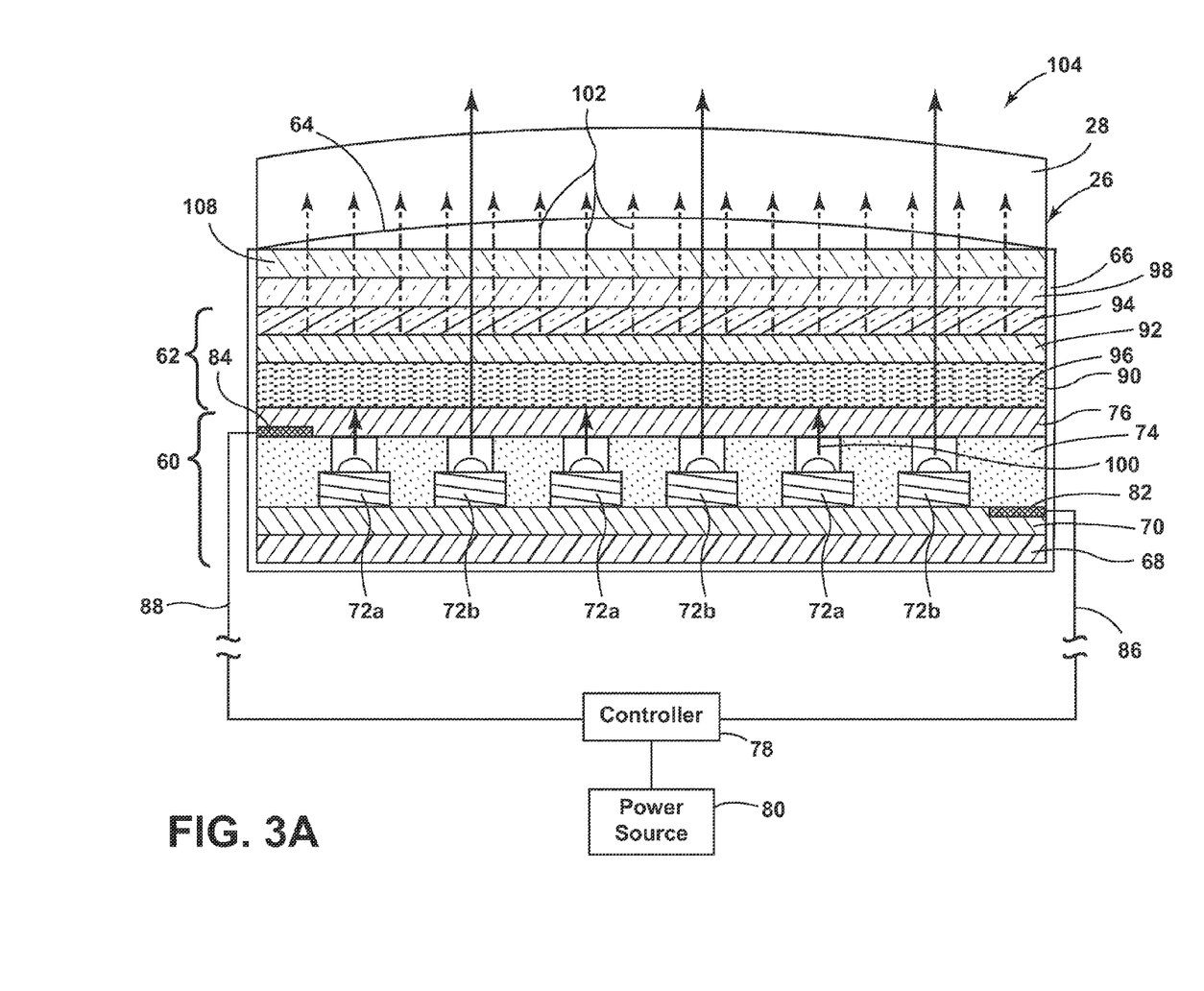
FIG. 3A is an enlarged view of section IIIA of FIG. 2A illustrating a light-producing-assembly, according to one embodiment.
Figure 3B:
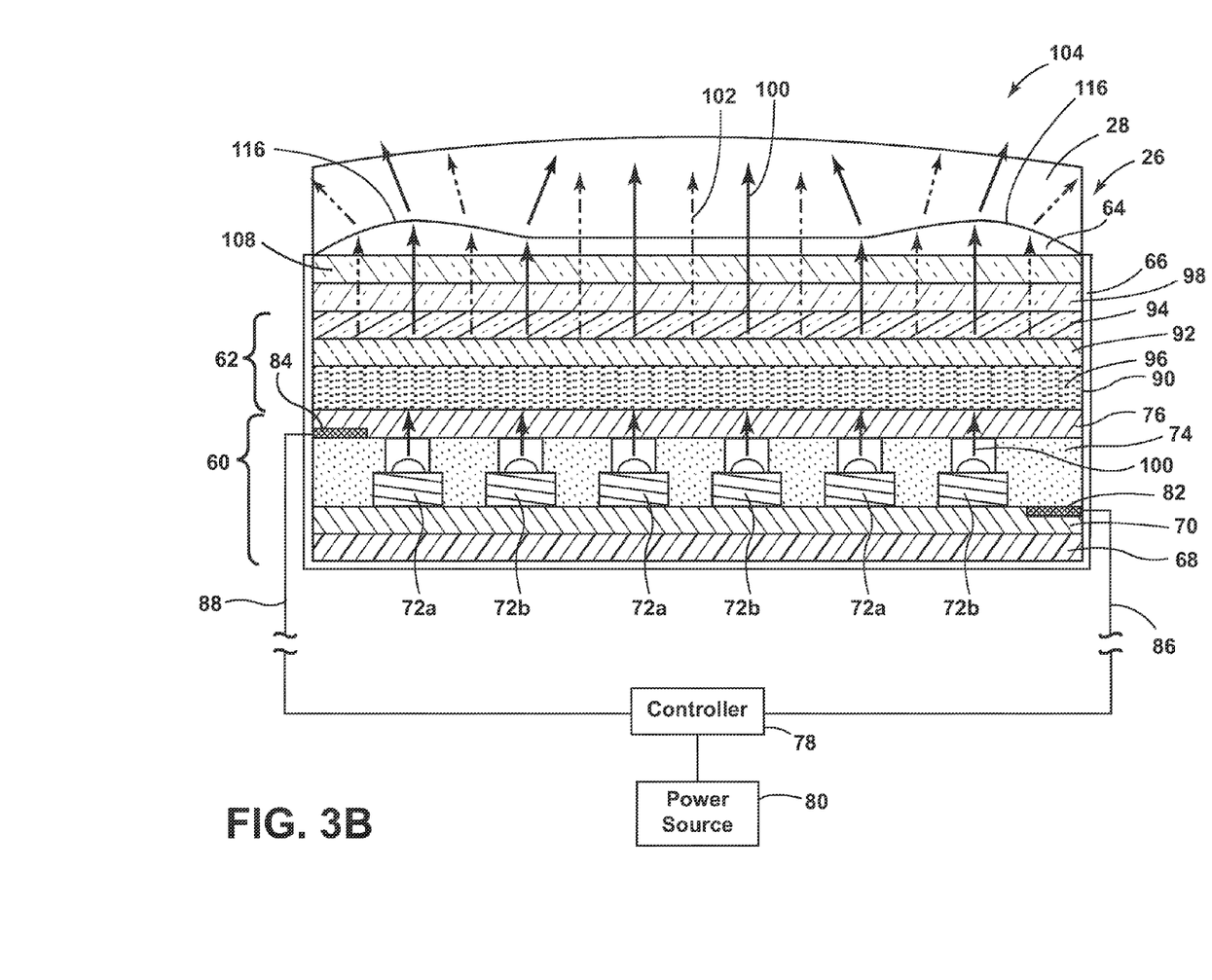
FIG. 3B is an enlarged of section IIIB of FIG. 2A illustrating an alternate light-producing-assembly, according to one embodiment.

Referring now to FIGS. 3A and 3B, the light-producing-assembly 26 may include a plurality of light emitting diodes (LEDs), or may include another form of light source. Depicted is a cross-sectional view of the light-producing-assembly 26 with an external photoluminescent structure 62, according to one embodiment. As illustrated in FIG. 3A, the light-producing-assembly 26 may have a stacked arrangement that includes a light source 60, a photoluminescent structure 62, a viewable portion 64, and an overmold material 66. It should be appreciated that the viewable portion 64 and the overmold material 66 may be two separate components, or may be integrally formed as a single component.

The light source 60 may correspond to a thin-film or printed light emitting diode (LED) assembly and includes a base member 68 as its lowermost layer. The base member 68 may include a polycarbonate, poly-methyl methacrylate (PMMA), or polyethylene terephthalate (PET) material, or any other material known in the art, in the range of about 0.005 to 0.060 inches thick and is arranged over the intended vehicle 10 surface on which the light-producing-assembly 26 is to be received (e.g., substrate 24). Alternatively, as a cost saving measure, the base member 68 may directly correspond to a preexisting vehicle structure (e.g., substrate 24). The light-producing-assembly 26 may be thermo-formed, or otherwise formed, to take the basic shape of the substrate 24 of the handle 16. Thereafter, the light-producing-assembly 26 may be insert molded or otherwise adhered to the substrate 24.

The light source 60 includes a positive electrode 70 arranged over the base member 68. The positive electrode 70 includes a conductive epoxy such as, but not limited to, a silver-containing or copper-containing epoxy. The positive electrode 70 is electrically connected to at least a first portion of a plurality of LED sources 72a and a second portion of a plurality of LEDs 72b arranged within a semiconductor ink 74 and applied over the positive electrode 70. Likewise, a negative electrode 76 is also electrically connected to at least a portion of the LED sources 72a, 72b. The negative electrode 76 is arranged over the semiconductor ink 74 and includes a transparent or translucent conductive material such as, but not limited to, indium tin oxide. Additionally, each of the positive and negative electrodes 70, 76 are electrically connected to a controller 78 and a power source 80 via corresponding bus bars 82, 84 and conductive leads 86, 88. The bus bars 82, 84 may be printed along opposite edges of the positive and negative electrodes 70, 76 and the points of connection between the bus bars 82, 84 and the conductive leads 86, 88 may be at opposite corners of each bus bar 82, 84 to promote uniform current distribution along the bus bars 82, 84. It should be appreciated that in alternate embodiments, the orientation of components within the light source 60 may be altered without departing from the concepts of the present disclosure. For example, the negative electrode 76 may be disposed below the semiconductor ink 74 and the positive electrode 70 may be arranged over the aforementioned semiconductor ink 74. Likewise, additional components, such as the bus bars 82, 84 may also be placed in any orientation such that the light source 60 may emit inputted light 100 towards a desired location.

The first portion of LED sources 72a and the second portion of LED sources 72b, may be dispersed in a random or controlled fashion within the semiconductor ink 74 and may be configured to emit focused or non-focused light toward the photoluminescent structure 62. The LED sources 72a, 72b may correspond to micro-LEDs of gallium nitride elements in the range of about 5 to about 400 microns in diameter, width, and/or length and the semiconductor ink 74 may include various binders and dielectric material including, but not limited to, one or more of gallium, indium, silicon carbide, phosphorous, and/or translucent polymeric binders.

The semiconductor ink 74 can be applied through various printing processes, including ink jet and silk screen processes, to selected portion(s) of the positive electrode 70. More specifically, it is envisioned that the portions of LED sources 72a, 72b are dispersed within the semiconductor ink 74, and shaped and sized such that a substantial quantity of the LED sources 72a, 72b align with the positive and negative electrodes 70, 76 during deposition of the semiconductor ink 74. The portion of the LED sources 72a, 72b that ultimately are electrically connected to the positive and negative electrodes 70, 76 may be illuminated by a combination of the bus bars 82, 84, controller 78, power source 80, and conductive leads 86, 88. According to one embodiment, the power source 80 may correspond to a vehicular power source 80 operating at 12 volts DC to 16 volts DC. When the portions of LED sources 72a, 72b are activated, they may emit light ranging from not visible (e.g., infrared, near-infrared, ultraviolet, and/or near-ultraviolet) to visible (e.g., violet, indigo, blue, green, yellow, orange, and/or red). Additional information regarding the construction of light-producing assemblies is disclosed in U.S. Patent Publication No. 2014/0264396 A1 to Lowenthal et al., entitled "ULTRA-THIN PRINTED LED LAYER REMOVED FROM SUBSTRATE," filed Mar. 12, 2014, the entire disclosure of which is incorporated herein by reference. The first portion of LED sources 72a may be configured to activate upon application of current across the light-producing-assembly 26 in a first direction and the second portion of LED sources 72b may be configured to activate upon the application of current across the light-producing-assembly 26 in a second direction. By configuring the first and second portions of LED sources 72a, 72b to be activated by differing directions of current application, the controller 78 may selectively choose which portion of LED sources 72a, 72b to activate based on the direction of current the controller 78 provides. It will be understood that in some embodiments the controller 78 may appear to be activating both portions of LED sources 72a, 72b by applying alternating current to the light source 60.

Referring still to FIG. 3A, the photoluminescent structure 62 is arranged over the negative electrode 76 as a coating, layer, film or other suitable deposition. With respect to the presently illustrated embodiment, the photoluminescent structure 62 may be arranged as a multi-layered structure including an energy conversion layer 90, optional stability layer 92, and optional protection layer 94.

The energy conversion layer 90 includes at least one photoluminescent material 96 having energy converting elements with phosphorescent or fluorescent properties. For example, the photoluminescent material 96 may include organic or inorganic fluorescent dyes including rylenes, xanthenes, porphyrins, phthalocyanines. Additionally, or alternatively, the photoluminescent material 96 may include phosphors from the group of Ce-doped garnets such as YAG:Ce. The energy conversion layer 90 may be prepared by dispersing the photoluminescent material 96 in a polymer matrix to form a homogenous mixture using a variety of methods. Such methods may include preparing the energy conversion layer 90 from a formulation in a liquid carrier medium and coating the energy conversion layer 90 to the negative electrode 76 or other desired base member 68 (e.g., substrate 24). The energy conversion layer 90 may be applied to the negative electrode 76 by painting, screen printing, flexography, spraying, slot coating, dip coating, roller coating, bar coating, and/or any other methods known in the art. Alternatively, the energy conversion layer 90 may be prepared by methods that do not use a liquid carrier medium. For example, the energy conversion layer 90 may be rendered by dispersing the photoluminescent material 96 into a solid state solution (homogenous mixture in a dry state) that may be incorporated in a polymer matrix formed by extrusion, injection seal, compression seal, calendaring, thermoforming, etc.

To protect the photoluminescent material 96 contained within the energy conversion layer 90 from photolytic and thermal degradation, the photoluminescent structure 62 may include the stability layer 92. The stability layer 92 may be configured as a separate layer optically coupled and adhered to the energy conversion layer 90 or otherwise integrated therewith. The photoluminescent structure 62 may also include the protection layer 94 optically coupled and adhered to the stability layer 92 or other layer (e.g., the energy conversion layer 90 in the absence of the stability layer 92) to protect the photoluminescent structure 62 from physical and chemical damage arising from environmental exposure. The stability layer 92 and/or the protection layer 94 may be combined with the energy conversion layer 90 through sequential coating or printing of each layer, sequential lamination or embossing, or any other suitable means. Additional information regarding the construction of photoluminescent structures is disclosed in U.S. Pat. No. 8,232,533 to Kingsley et al., entitled "PHOTOLYTICALLY AND ENVIRONMENTALLY STABLE MULTILAYER STRUCTURE FOR HIGH EFFICIENCY ELECTROMAGNETIC ENERGY CONVERSION AND SUSTAINED SECONDARY EMISSION," filed Nov. 8, 2011, the entire disclosure of which is incorporated herein by reference.

In operation, the photoluminescent material 96 is formulated to become excited upon receiving inputted light 100 of a specific wavelength from at least a portion of the LED sources (e.g., the first or second portions 72a, 72b) of the light source 60. As a result, the inputted light 100 undergoes an energy conversion process and is re-emitted at a different wavelength. It will be understood that not all of the inputted light 100 may be converted and that a portion of the inputted light 100 may pass through the photoluminescent structure 62. According to one embodiment, the photoluminescent material 96 may be formulated to convert inputted light 100 into a longer wavelength light (e.g., from blue light to red light), otherwise known as down conversion. Alternatively, the photoluminescent material 96 may be formulated to convert inputted light 100 into a shorter wavelength light (e.g., red light to blue light), otherwise known as up conversion. Under either approach, light converted by the photoluminescent material 96 may be immediately outputted 102 from the photoluminescent structure 62 or otherwise used in an energy cascade, wherein the converted light serves as inputted light to excite another formulation of photoluminescent material 96 located within the energy conversion layer 90, whereby the subsequent converted light may then be outputted from the photoluminescent structure 62 or used as inputted light, and so on. With respect to the energy conversion processes described herein, the difference in wavelength between the inputted light 100 and the converted outputted light 102 is known as the Stokes shift and may serve as the principle driving mechanism for an energy conversion process corresponding to a change in wavelength of light.

With continued reference to FIG. 3A, the viewable portion 64 is arranged over the photoluminescent structure 62. In some embodiments, the viewable portion 64 may include a plastic, silicon, or urethane material and is molded over the photoluminescent structure 62 and light source 60. Preferably, the viewable portion 64 should be at least partially light transmissible. In this manner, the viewable portion 64 will be illuminated by the photoluminescent structure 62 whenever an energy conversion process is underway. Additionally, by over-sealing the viewable portion 64, it may also function to protect the photoluminescent structure 62 and the light source 60. The viewable portion 64 may be arranged in a planar shape and/or an arcuate shape to enhance its viewing potential when in a luminescent state. Like the photoluminescent structure 62 and the light source 60, the viewable portion 64 may also benefit from a thin design, thereby helping to fit the light-producing-assembly 26 into small package spaces of the vehicle 10 (e.g., the handle assembly 14 or other commonly touched locations of the vehicle 10).

In some embodiments, a decorative layer 98 may be disposed between the viewable portion 64 and the photoluminescent structure 62. The decorative layer 98 may include a polymeric material, or other suitable material and is configured to control or modify an appearance of the viewable portion 64 of the light source 60. For example, the decorative layer 98 may be configured to confer a reflective appearance to the viewable portion 64 when the viewable portion 64 is in an unilluminated state. In various embodiments, the decorative layer 98 may be optional if used in conjunction with the hiding layer 28 or the decorative layer 98 and the hiding layer 28 may cooperate to conceal or hide the light source 60 and/or light-producing-assembly 26. In other embodiments, the decorative layer 98 may be tinted any color to complement the vehicle structure on which the light source 60 is to be received. For example, the decorative layer 98 may be similar in color to that of the handle 16 (FIG. 1) so that the light source 60 and/or the light-producing-assembly 26 is substantially hidden when in the unilluminated state. Alternatively, the decorative layer 98 may provide indicia and/or an emblem such that the decorative layer 98 and the indicia may be backlit and/or otherwise illuminated by the light source 60. In any event, the decorative layer 98 should be at least partially light transmissible such that the photoluminescent structure 62 is not prevented from illuminating the viewable portion 64 whenever an energy conversion process is underway.

The overmold material 66 is disposed around the light source 60 and photoluminescent structure 62 and may be formed integrally with the viewable portion 64. The overmold material 66 may protect the light source 60 from physical and chemical damage arising from environmental exposure. The overmold material 66 may have viscoelasticity (i.e., having both viscosity and elasticity), a low Young's modulus, and/or a high failure strain compared with other materials, so that the overmold material 66 may protect the light source 60 when contact is made thereto. For example, the overmold material 66 may protect the light source 60 from the damaging contact that may occur when the handle assembly 14 (FIG. 1) is actuated. It will be understood that the use of the overmold material 66 may be optional when used in conjunction with the hiding layer 28 or that the overmold material 66 and the hiding layer 28 may be combined without departing from the spirit of this disclosure.

In some embodiments, the photoluminescent structure 62 may be employed separate and away from the light source 60. For example, the photoluminescent structure 62 may be positioned on a vehicle component or surface proximate (e.g., the protective layer 30 and/or the hiding layer 28), but not in physical contact with, the light source 60, as will be described in more detail below. It should be understood that in embodiments where the photoluminescent structure 62 is incorporated into distinct components separated from the light source 60, the light source 60 may still have the same or similar structure to the light source 60 described in reference to FIG. 3A.

Still referring to FIG. 3A, an energy conversion process 104 for generating multiple colors of light is illustrated, according to one embodiment. In this embodiment, the energy conversion layer 90 includes the photoluminescent material 96 that is interspersed within the energy conversion layer 90 and a phosphorescent structure 108. Alternatively, the photoluminescent materials 96 and the phosphorescent structure 108 may be combined to form a single layer. It will be understood that the energy conversion layer may contain multiple photoluminescent materials, each having a different absorption spectrum that leads to a different Stokes shift allowing for the production of multiple colors of outputted light 102. Further, in various embodiments, the absorption spectrums of the different photoluminescent materials may be tailored to create a cascade effect where the emission of one photoluminescent material excites another photoluminescent material. The phosphorescent structure 108 may include any of the phosphorescent materials described above. In one embodiment, the energy conversion process 104 occurs by way of down conversion using blue, violet, and/or UV light as the source of excitation.

According to one exemplary embodiment, the first portion of the LED sources 72a is configured to emit the inputted light 100 having an emission wavelength that only excites photoluminescent material 96 (e.g., blue light having a wavelength of about 470 nm) and results in the inputted light 100 being converted into a visible outputted light 102 of a first color (e.g., blue). Likewise, the second portion of the LED sources 72b is configured to emit the inputted light 100 having an emission wavelength that excites only the phosphorescent structure 108 (e.g., ultraviolet light) and the disinfecting layer 32 and results in the inputted light 100 being converted into a visible outputted light 102 of a second color (e.g., red) while the disinfecting layer 32 is activated. Preferably, the first and second colors are visually distinguishable from one another. In this manner, LED sources 72a and 72b may be selectively activated using the controller 78 to cause the photoluminescent structure 62 to luminesce and the phosphorescent structure 108 to phosphoresce in different colors from one another such that it can be quickly determined if the disinfecting layer 32 is active based on the color of the viewable portion 64. For example, the controller 78 may activate only LED sources 72a to exclusively excite the photoluminescent material 96, resulting in the viewable portion 64 illuminating in the first color. Alternatively, the controller 78 may activate only LED sources 72b to exclusively excite the phosphorescent structure 108, resulting in the viewable portion 64 illuminating in the second color while activating the disinfecting layer 32.

Alternatively still, the controller 78 may activate LED sources 72a and 72b in concert, which causes both of the photoluminescent material 96 and the phosphorescent structure 108 to become excited, resulting in the viewable portion 64 illuminating in a third color, which is a color mixture of the first and second color (e.g., purple). The intensities of the inputted light 100 emitted from each light source 72a, 72b may also be proportionally varied to one another such that additional colors may be obtained. For energy conversion layers 90 containing more than two distinct photoluminescent materials, a greater diversity of colors may be achieved. Contemplated colors include red, green, blue, and combinations thereof, including white, all of which may be achieved by selecting the appropriate photoluminescent materials and correctly manipulating the corresponding LED sources 72a, 72b.

Referring to FIG. 3B, the light-producing-assembly 26 may also include optics 116 that are configured to direct inputted light 100 emitted from the LED sources 72a, 72b and the outputted light 102 emitted from the photoluminescent structure 62 and the phosphorescent structure 108 towards pre-defined locations. For example, the inputted light 100 emitted from the LED sources 72a, 72b and the photoluminescent structure 62 may be directed and/or focused towards a desired feature and/or location on the handle assembly 14 or proximate the handle assembly 14.

Figure 4:
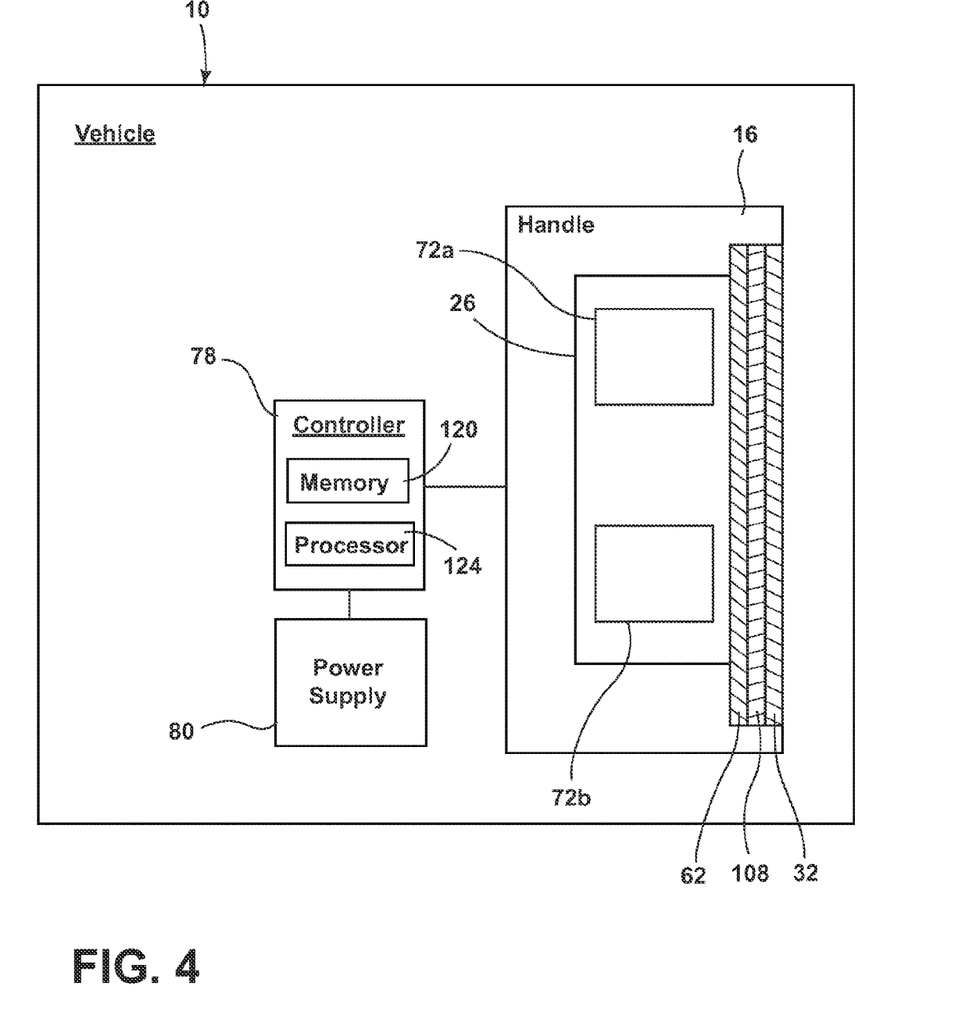
FIG. 4 is a block diagram further illustrating the handle assembly.

Referring now to FIG. 4, a box diagram of the vehicle 10 is shown in which a disinfecting handle 16 is implemented. The vehicle 10 includes the controller 78 in communication with the disinfecting handle 16. The controller 78 may include a memory 120 having instructions contained therein that are executed by a processor 124 of the controller 78. The controller 78 may provide electrical power to the handle 16 and the light-producing-assembly 26 via the power source 80 located onboard the vehicle 10. In addition, the controller 78 may be configured to control the light output of the light-producing-assembly 26 based on feedback received from one or more vehicle control modules. The control module 78 may be configured to operate the first portion of LEDs 72a and the second portion of LEDs 72b separately and/or in an alternating manner (e.g., via current direction manipulation). In embodiments where the first portion of LEDs 72a are configured to emit light and the second portion of LEDs 72b are configured to emit ultraviolet light, the controller 78 may independently control when the disinfecting layer 32 of the handle 16 is activated (e.g., by applying ultraviolet light to the disinfecting layer 32) and when the handle assembly 14 (FIG. 1) emits a first color (e.g., by emitting light of a desired wavelength or by exciting the photoluminescent structure 62). For example, the controller 78 may illuminate the handle assembly 14 and generally the interior 22 (FIG. 1) of the vehicle 10 in a first color (e.g., blue light emitted either from the first portion of LEDs 72a or from the photoluminescent structure 62) to indicate that the handle 16 is not being disinfected, and activate the second portion of LEDs 72b which may emit ultraviolet light configured to excite the phosphorescent structure 108 to glow in a different color than the photoluminescent structure 62 and to activate the disinfecting layer 32. In this way, occupants of the vehicle 10 may know if the disinfecting layer 32 is active or not simply by observing the color of the handle assembly 14. The controller 78 may be configured to activate the disinfecting layer 32 of the handle 16 after predetermined periods of time, after the controller 78 senses that the door 12 has been opened and/or closed, after the controller 78 senses the handle 16 has been touched (e.g., via capacitive sensing or other methods) and/or when the controller 78 detects dirt, oil, or pathogens on the surface of or proximate the handle 16.

Use of the handle 16 and/or handle assembly 14, as described herein, may offer several advantages. For example, illuminating the handle 16 of the handle assembly 14 may make it easier for an occupant of the vehicle 10 to locate the handle 16 in low lighting conditions. Additionally, the illumination of the handle 16 allows for a variety of lighting effects to be achieved within the interior 22 of the vehicle 10 such as ambient lighting, effects lighting (e.g., pulsing with music), safety lighting and/or aesthetic lighting. The disinfecting properties of the handle 16 may decrease the transmission of pathogens between occupants, decrease the need to clean the handle 16 and/or prevent the transmission of contaminants from the hand of one occupant to another. Further, by providing different lighting for active and non-active states of the handle 16, the occupant may easily determine if the handle 16 has been disinfected while providing a clear message to the occupant that the handle 16 is being disinfected which may delight the occupant. While the handle assembly 14 and handle 16 are contemplated for use in automobiles, it should be appreciated that the handle 16 and handle assembly 14 provided herein may be similarly used in other types of vehicles designed to transport one or more passengers such as, but not limited to, aircraft, watercraft, and locomotives. Further, it will be understood that this disclosure may equally be applied to non-vehicle applications such as building door handles, shopping carts, appliance handles, restroom fixtures, hand held remote controls and/or table tops.

For the purposes of describing and defining the present teachings, it is noted that the terms "substantially" and "approximately" are utilized herein to represent the inherent degree of uncertainty that may be attributed to any quantitative comparison, value, measurement, or other representation. The term "substantially" and "approximately" are also utilized herein to represent the degree by which a quantitative representation may vary from a stated reference without resulting in a change in the basic function of the subject matter at issue.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:
1. A vehicle handle assembly comprising:
a light-producing-assembly comprising, a first light source, and
a second light source, wherein the first and second light sources are configured to emit light of different wavelengths;
a photoluminescent structure configured to luminesce in response to excitation by light emitted by the first light source; and
a disinfecting layer configured to activate in response to excitation by light from the second light source for disinfecting the vehicle handle assembly.

2. The vehicle handle assembly of claim 1, wherein the second light source is configured to emit ultraviolet light.

3. The vehicle handle assembly of claim 2, further comprising:
a hiding layer positioned between the light-producing-assembly and the disinfecting layer.

4. The vehicle handle assembly of claim 1, further comprising:
a protective layer positioned between the disinfecting layer and the light-producing-assembly.

5. The vehicle handle assembly of claim 1, wherein the light emitted from the second light source is configured to not excite the photoluminescent structure.

6. The vehicle handle assembly of claim 1, wherein the first light source is a first portion of LEDs and the second light source is a second portion of LEDs and the light producing assembly is configured to emit light toward an interior of a vehicle.

7. A vehicle handle assembly comprising:
a substrate;
a light-producing-assembly comprising first LEDs and second LEDs, the first LEDs configured to emit light of a different wavelength than the second LEDs; and
a disinfecting layer activated based on light of at least one of the first and second LEDs for disinfecting the vehicle handle assembly.

8. The handle assembly of claim 7, further comprising:
a protective layer, wherein the protective layer is positioned between the disinfecting layer and the light-producing-assembly.

9. The handle assembly of claim 8, wherein the disinfecting layer comprises $TiO_2$.

10. The handle assembly of claim 7, wherein the first LEDs are configured to emit light toward the disinfecting layer.

11. The handle assembly of claim 7, wherein the second LEDs are configured to emit light of a wavelength which activates the disinfecting layer.

12. The handle assembly of claim 11, wherein the first LEDs are configured to emit light of a wavelength which does not activate the disinfecting layer.

13. The handle assembly of claim 12, further comprising:
a photoluminescent structure, wherein the light from the first LEDs is configured to activate the photoluminescent structure and light from the second LEDs is configured to not activate the photoluminescent structure.

14. A method of disinfecting a vehicle handle comprising the steps of:
providing the vehicle handle comprising a light-producing-assembly having first LEDs and second LEDs;
energizing a disinfecting layer and a phosphorescent structure using light from the second LEDs; and
altering a direction of electrical current across the light-producing-assembly to activate the first LEDs and deactivate the second LEDs.

15. The method of claim 14, wherein activation of the first LEDs excites a photoluminescent structure.

16. The method of claim 15, wherein activation of the second LEDs excites a phosphorescent structure.

17. The method of claim 14, wherein altering the direction of electrical current across the light-producing-assembly changes a color of light emitted from the disinfecting handle.

18. The method of claim 15, wherein the disinfecting layer comprises $TiO_2$ and the second LEDs are configured to emit ultraviolet light.

19. The method of claim 15, wherein the disinfecting layer is positioned on a protective layer.

* * * * *